United States Patent [19]
Kaplan

[11] Patent Number: 5,619,997
[45] Date of Patent: Apr. 15, 1997

[54] PASSIVE SENSOR SYSTEM USING ULTRASONIC ENERGY

[75] Inventor: Shay Kaplan, Givat Elah, Israel

[73] Assignee: Mizur Technology Ltd., Givat Elah, Israel

[21] Appl. No.: 379,396

[22] Filed: Jan. 27, 1995

[30] Foreign Application Priority Data

Jan. 28, 1994 [IL] Israel .......................................... 108470

[51] Int. Cl.⁶ .............................. A61B 8/00; G01K 11/22; G01N 11/10
[52] U.S. Cl. ..................................... 128/660.02; 73/54.41; 128/7.36; 374/117
[58] Field of Search ...................... 374/117; 128/660.01, 128/600.02, 662.03; 73/54.01, 54.224, 54.41, 54.42

[56] References Cited

U.S. PATENT DOCUMENTS

| | | | |
|---|---|---|---|
| 3,853,117 | 12/1974 | Murr | 128/660.02 |
| 4,265,251 | 5/1981 | Tickner | 128/660.02 |
| 4,513,750 | 4/1985 | Heyman et al. | 128/660.02 |
| 5,195,520 | 3/1993 | Schlief et al. | 128/660.02 |

OTHER PUBLICATIONS

W.K. Schomburg, et al., "Mikromembranen für berührugslose Messungen mit Ultraschall", VDI Berichte No. 939, 1992.

English Translation of W.K. Schomburg, et al., "Micromembranes for Contactless Measurements Using Ultrasound", VDI Berichte No. 939, 1992.

Primary Examiner—Francis Jaworski
Attorney, Agent, or Firm—Wilson Sonsini Goodrich & Rosati

[57] ABSTRACT

A passive sensor system utilizing ultrasonic energy is disclosed. The passive sensor system includes at least one ultrasonically vibratable sensor and an ultrasonic activation and detection system. The sensor has at least one vibration frequency which is a function of a physical variable to be sensed. The ultrasonic activation and detection system excites the sensor and detects the vibration frequency from which it determines a value of the physical variable. The sensor includes a housing, a membrane which is attached to the housing and which is responsive to the physical variable, a vibratable beam attached to the housing at one end and a coupler, attached to the membrane and to a small portion of the vibratable beam, which bends the vibratable beam in response to movement of the membrane.

10 Claims, 3 Drawing Sheets

PASSIVE SENSOR SYSTEM USING ULTRASONIC ENERGY

FIELD OF THE INVENTION

The present invention relates to passive sensors in general and to ultrasonic passive sensors in particular.

BACKGROUND OF THE INVENTION

Passive sensors (for implanting into the human body or for mounting at some inaccessible location within a machine) are known in the art. These sensors are typically electromagnetic, providing an electromagnetic signal when activated.

The prior art sensor system typically comprises a sensor, implanted into the machine, and an activating and detecting system. The sensor is typically an oscillating circuit whose vibration frequency changes in response to the physical variable to be measured. The oscillating circuit typically includes a capacitor and an inductor, one of which is built to vary in accordance with the physical variable being measured. As a result, the vibration frequency of the circuit is a function of the physical variable.

When the sensor is irradiated with electromagnetic energy from the activating system, some of the energy is absorbed by the oscillating circuit, depending on how close the incident frequency or frequencies are to the resonant frequency of the circuit (which, in turn, depends on the physical variable being measured). The change in the electromagnetic field due to the absorption of energy by the oscillating circuit is detected by the detecting system.

Electromagnetic sensors and systems are described in the U.S. Pat. No. 4,127,110 and in the article:

Carter C. Collins, "Miniature Passive Pressure Transensor for Implanting in the Eye", *IEEE Transactions on Bio-Medical Engineering*, Vol. BME-14, No. 2, April 1967.

Unfortunately, within living tissue, the passive sensor is detectable within a range no larger than 10 times the diameter of its antenna (part of the oscillating circuit). Furthermore, the sensor system is not operative within a conductive enclosure.

SUMMARY OF THE PRESENT INVENTION

It is therefore an object of the present invention to provide a passive sensor system which has none of the disadvantages listed hereinabove.

The present invention provides a passive sensor system utilizing ultrasonic energy. The passive sensor includes a vibratable element whose vibration frequency changes in response to physical variables (such as pressure, temperature, etc.). The external activating and detecting system includes an ultrasonic transducer which transmits an ultrasonic wave, having a range of frequencies, to the passive sensor which resonates in response only if the ultrasonic waves includes in it the current vibration frequency of the vibratable element.

Since the present invention utilizes ultrasonic waves, its range, at frequencies lower than 1 MHz, is sufficient for use in humans. Furthermore, the sensor is operative within conductive enclosures.

In accordance with a preferred embodiment of the present invention, the ultrasonic activation and detection system includes a) an ultrasonic wave generator for generating an ultrasonic wave having a desired frequency band, b) an ultrasonic transducer system for transmitting the ultrasonic wave and for receiving an ultrasonic wave in response and c) a frequency detector for detecting the vibration frequency of the sensor from the received ultrasonic wave.

Moreover, in accordance with a preferred embodiment of the present invention, the passive sensor has excitation and transmission frequencies. Additionally, the sensor can have a reference vibration frequency.

In accordance with one embodiment of the sensor, it includes a) a housing, b) a membrane attached to the housing and responsive to the physical variable, c) a vibratable beam attached to the housing at one end and d) a coupler, attached to the membrane and to a small portion of the vibratable beam, which bends the vibratable beam in response to movement of the membrane.

In accordance with another embodiment of the sensor, the vibratable beam is attached at two ends and the coupler divides the beam into two separate but coupled vibratable beams vibratable at the excitation and transmission frequencies.

Moreover, in accordance with a further preferred embodiment of the present invention, the sensor includes a) a first cup shaped body having a flat base formed of a thin membrane vibratable at the excitation frequency and b) a second cup shaped body having a flat base formed of a thick membrane vibratable at the transmission frequency. The first and second bodies are joined together so as to produce an enclosed space between them.

Finally, in accordance with a still further preferred embodiment of the present invention, the sensor system includes a plurality of ultrasonically vibratable sensors each having a common input vibration frequency range and at least one output vibration frequency. The ultrasonic activation and detection system transmits an ultrasonic wave having frequencies within the input frequency range and detects the separate output vibration frequencies.

BRIEF DESCRIPTION OF THE DRAWINGS

The present invention will be understood and appreciated more fully from the following detailed description taken in conjunction with the drawings in which:

FIGS. 3A and 3B are schematic illustrations of an alternative sensor having two coupled vibrating beams and a reference beam, wherein FIG. 3A is a side view and FIG. 3B is a top view taken along lines IIIB—IIIB of FIG. 3A;

DETAILED DESCRIPTION OF A PREFERRED EMBODIMENT

Figure 1:
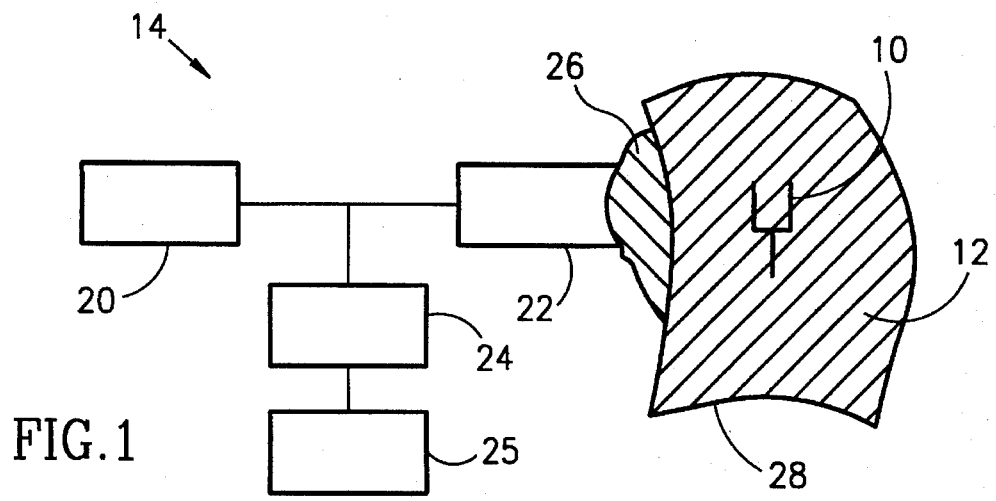
FIG. 1 is a schematic illustration of an ultrasonic passive sensor system, constructed and operative in accordance with a preferred embodiment of the present invention.

Reference is now made to FIG. 1 which illustrates the ultrasonic sensor system of the present invention. The system comprises a passive sensor 10 and an external ultrasonic activation and detection system 14. The sensor 10 is implantable in an ultrasound compatible medium 12, such as the human body, or mountable on an inner wall of an enclosure.

The sensor 10 is any suitable sensor, examples of which are described hereinbelow with respect to FIGS. 2–4, which mechanically vibrates in the presence of an ultrasonic wave, much as a tuning fork vibrates in the presence of a sonic wave. Therefore, sensor 10 is represented schematically in FIG. 1. as a tuning fork. The frequency of vibration of sensor 10 is its current vibration frequency which is a function at least of the physical variable being sensed.

The activation and detection system 14 typically comprises an ultrasonic generator 20, at least one ultrasonic transducer 22, a frequency detector 24 and a data processor 25. The ultrasonic generator 20 and transducer 22 constitute the activating elements and the transducer 22, the frequency detector 24 and the data processor 25 constitute the detecting elements.

The generator 20, such as the non destructive testing unit, model IIB USDF, manufactured by Balteu Sonatest/Schlumberger of Milton Keynes, England, generates an ultrasonic wave to be transmitted by the ultrasonic transducer 22 to the sensor 10 via the medium 12. Typically, ultrasonic gel 26, located on an outer edge 28 of medium 12, is utilized to couple the transducer 22 to the medium 12. Typically, the transmitted ultrasonic wave is composed of a single frequency or a range of frequencies.

The ultrasonic transducer 22, such as one part of the non-destructive testing unit, typically also receives ultrasonic waves from the medium 12. Some of these waves are reflections of the transmitted wave; others are from sensor 10. In an alternative embodiment, there are two ultrasonic transducers 22, one for transmitting and one for receiving.

If the transmitted ultrasonic waves have a frequency close or equivalent to the current vibration frequency of the sensor 10, they will excite the sensor 10 to vibrate, in effect, absorbing at least some of the transmitted wave at the current vibration frequency. Thus, the waves received by transducer 22 include less of the current vibration frequency of sensor 10 than of other frequencies. In addition, the sensor 10 continues to vibrate even after transmission of ultrasonic waves has stopped. Thus, the transducer 22 continues to receive ultrasonic waves and these are at the current vibration frequency of sensor 10.

The frequency detector 24, similar to the 8590A spectrum analyzer manufactured by Hewlett Packard Inc. of the U.S.A., analyzes the received ultrasonic waves to determine which frequency has been absorbed by sensor 10 and/or at which frequency the sensor 10 resonates when no longer excited by the transmitted ultrasonic waves.

Data processor 25 converts the frequency determined by the frequency detector 24 into the value of the physical variable being measured. The information needed for this conversion depends on the actual structure of the sensor 10, as described in more detail hereinbelow.

It will be appreciated that the system of the present invention is implantable deep within living tissue or within a conductive enclosure. The system operates with mechanical vibration rather than electromagnetic resonance.

Figure 2A:
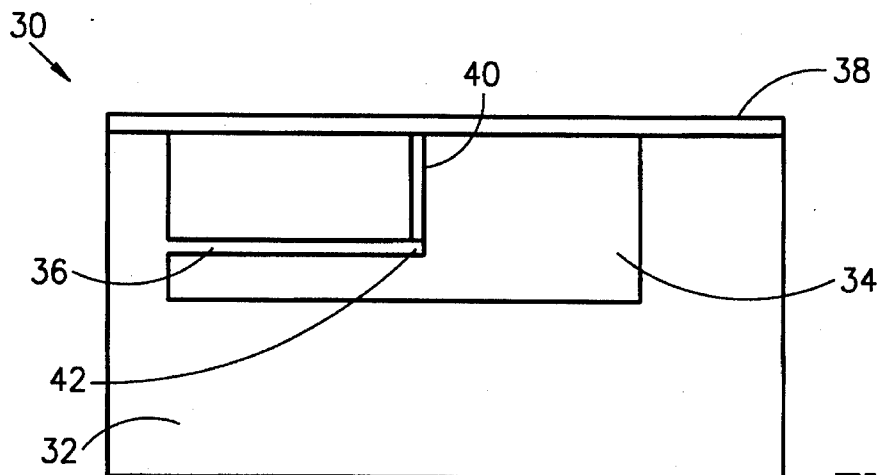
FIG. 2A is a schematic illustration of an passive sensor useful in the sensor system of FIG. 1.
Figure 2B:
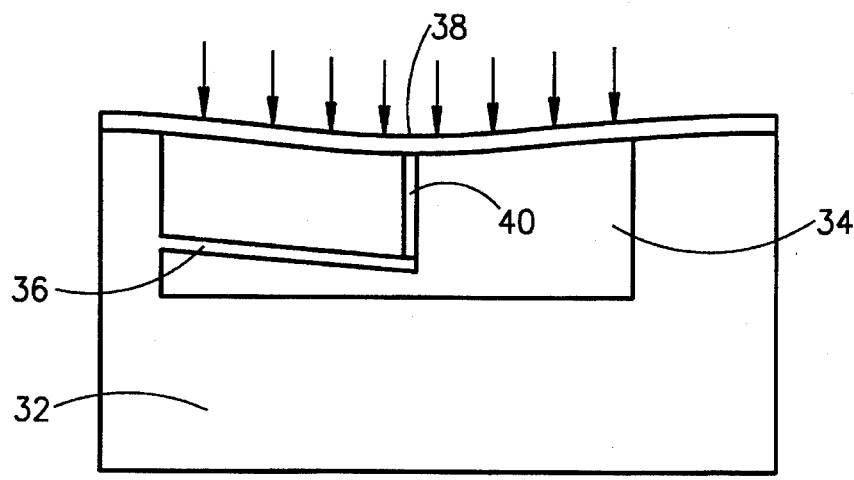
FIG. 2B is a schematic illustration of the sensor of FIG. 2A in the presence of pressure.

Reference is now made to FIGS. 2A and 2B which illustrate a first embodiment of an exemplary passive sensor, labeled 30, responsive to pressure. FIGS. 2A and 2B illustrate the sensor 30 in the absence and presence, respectively, of pressure.

Sensor 30 is typically machined from silicon and typically comprises a cup-shaped housing 32 having a recess 34, a vibratable beam 36, a membrane 38 and a coupler 40. The vibratable beam 36 is typically integrally attached to the housing 32 and extends into recess 34. The coupler 40 typically connects between membrane 38 and a far end 42 of beam 36. The coupler 40 is either integrally attached to the membrane 38 or the vibratable beam 36.

As shown in FIG. 2B, membrane 38 typically bends into recess 34 in response to pressure from the outside. This causes coupler 40, which is stiff, to press on far end 42, inducing beam 36 to bend and thus, straining it. As is known in the art, a strained beam vibrates at a higher frequency than a non-strained beam. Thus, the higher the pressure on membrane 38, the higher the vibration frequency of beam 36. The specific relationship between pressure and frequency of beam 36 depends on the material of beam 36, its length and its cross-sectional area and to some extent on other factors, such as temperature and viscosity of whatever medium is within recess 34.

It is noted that, if the membrane was made of many materials or coated with other materials, it would bend in response to other physical variables, such as temperature. For example, FIG. 2C illustrates a sensor responsive to temperature and FIG. 4B, described hereinbelow, illustrates a sensor responsive to chemical composition.

Figure 2C:
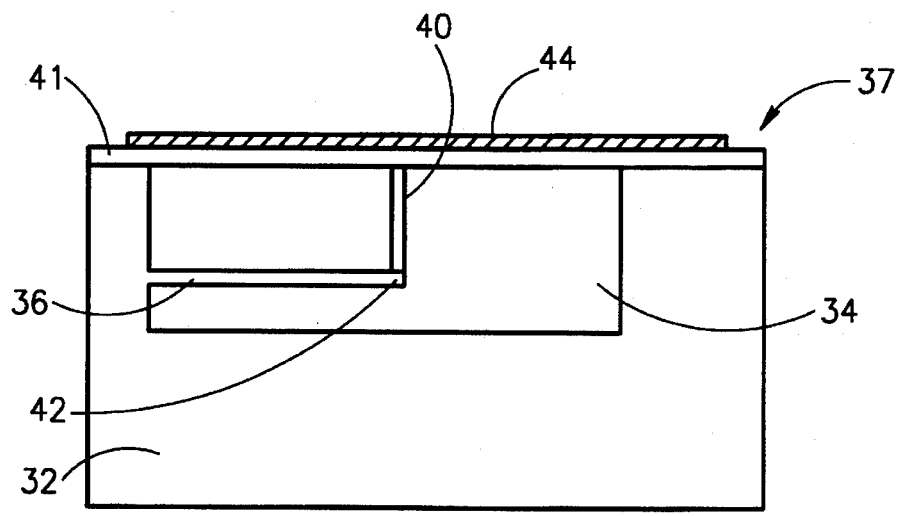
FIG. 2C is a schematic illustration of a sensor, similar to that of FIG. 2A, which is sensitive to temperature.

Reference is now briefly made to FIG. 2C. In this sensor, the membrane 37 is made of two materials, 41 and 44, each having different thermal coefficients. Exemplary materials are silicon and silicon nitride. Since the materials expand and contract at different rates, the membrane 37 will buckle as a function of the temperature.

Figure 3A:
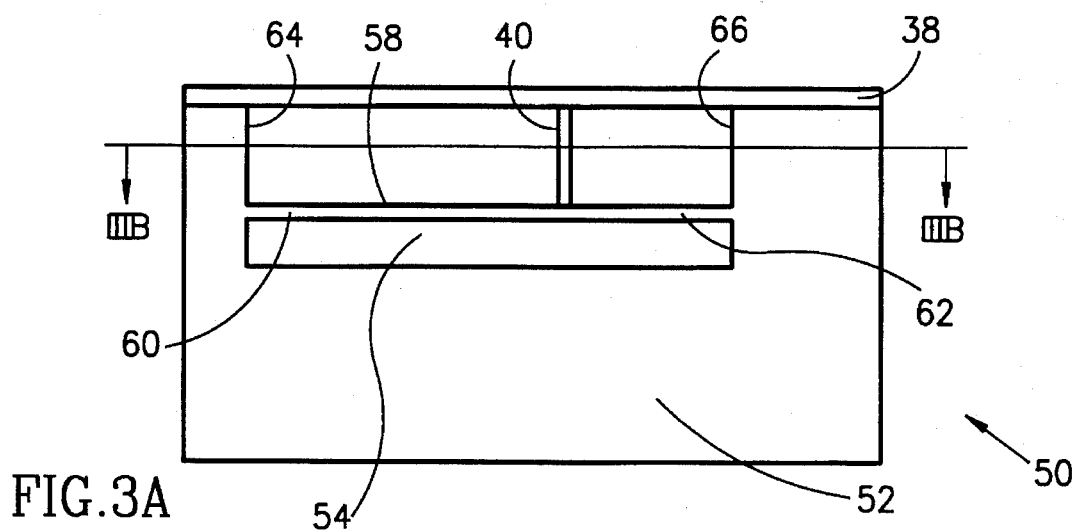
Figure 3B:
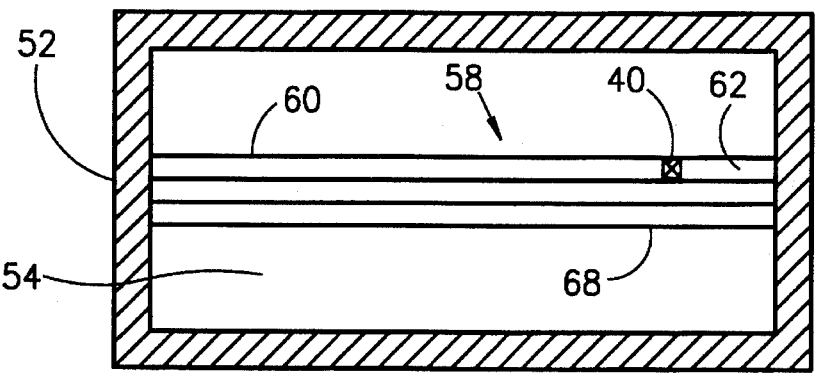

Reference is now made to FIGS. 3A and 3B which illustrate an alternative embodiment of the passive sensor which has different transmission and reception frequencies. Furthermore, the sensor of FIGS. 3A and 3B also has a reference frequency. FIG. 3A is a side view of the sensor, labeled 50, and FIG. 3B is a top view taken along lines IIIB—IIIB of FIG. 3A.

The sensor 50 is similar to sensor 30 (FIG. 2) in that it has a housing, labeled 52, and a recess 54. However, the vibratable element of sensor 50 is a full length beam 58. Similar to sensor 30, sensor 50 also has a membrane 38 and a coupler 40. In this embodiment, coupler 40 is connected to beam 58 somewhere other than at its middle so as to create two separate but coupled vibratable beams 60 and 62 which vibrate at different frequencies.

As illustrated in FIG. 3A, beam 60, defined as the length of beam 58 from a left edge 64 of housing 52 to coupler 40, is longer than beam 62, defined as the length of beam 58 from a right edge 66 of housing 52 to coupler 40. Therefore, beam 60 vibrates at a lower frequency than beam 62.

In the presence of pressure, membrane 38 bends, pushing coupler 40 further into recess 54 and bending beam 58, straining both beams 60 and 62. When in operation, the sensor system of the present invention excites sensor 50 with an ultrasonic wave whose range of frequencies is approximately the range of vibration frequencies of long beam 60. The long beam 60 becomes excited and its excitation causes short beam 62 also to vibrate, but at its current vibration frequency.

Since the short beam 62 typically has a vibration frequency range significantly different than that of the long beam 60, the ultrasonic transducer 22 and frequency detector 24 need only be tuned, for reception purposes, to the frequency range of short beam 62. Since only the short beam 62 will be active in its frequency range, the signal to noise (S/N) ratio of the signal received by the transducer 22 will be high since there will be little or no noise associated with the excitation frequency.

The sensor 50 can optionally also include a reference beam 68 (FIG. 3B), located next to beam 58. Beam 68 is connected at both ends to housing 52 but is not connected to coupler 40. Therefore, the vibration frequency of beam 68 does not change with pressure. Any changes of its vibration frequency must therefore be due to other causes, such as temperature, viscous damping, etc., which also affect the beams 60 and 62. The output of reference beam 68 is thus utilized, by data processor 25, to correct the pressure values determined from beams 60 and 62.

Figure 4A:
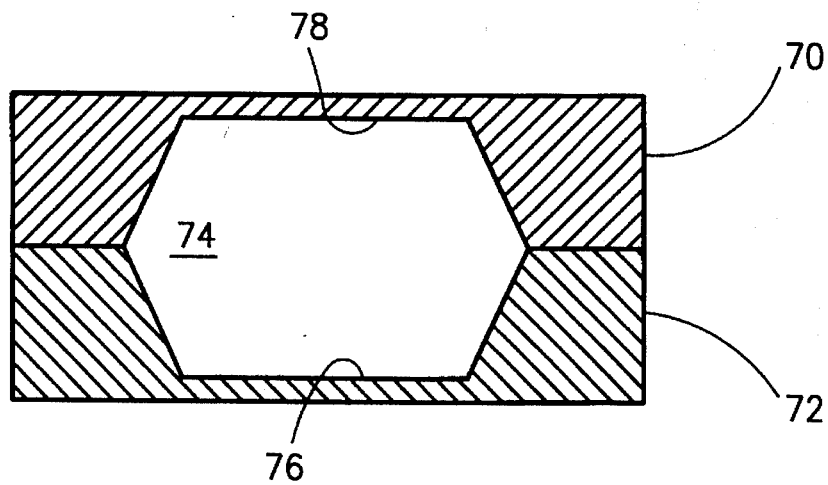
FIG. 4A is a schematic illustration of an alternative two membrane sensor.

Reference is now briefly made to FIG. 4A which illustrates a further alternative embodiment of the sensor formed of two silicon wafers 70 and 72. Typically, each wafer is formed into roughly a squared off cup shape and the two are bonded together so as to produce an enclosed space 74. The base of each cup is flat, forming a membrane which can freely vibrate into space 74. In order to provide the sensor of FIG. 4A with two different, coupled frequencies, the thickness of the membranes, labeled 76 and 78, is different.

As in the embodiment of FIG. 3A, the vibrating element with the lower vibration frequency, (i.e. thin membrane 78) receives the ultrasonic signal and the other membrane, thick membrane 76, transmits the reflected ultrasonic signal. The two vibrating elements are coupled via the sides of the wafers 70 and 72 and through whatever medium is placed into enclosed space 74.

Figure 4B:
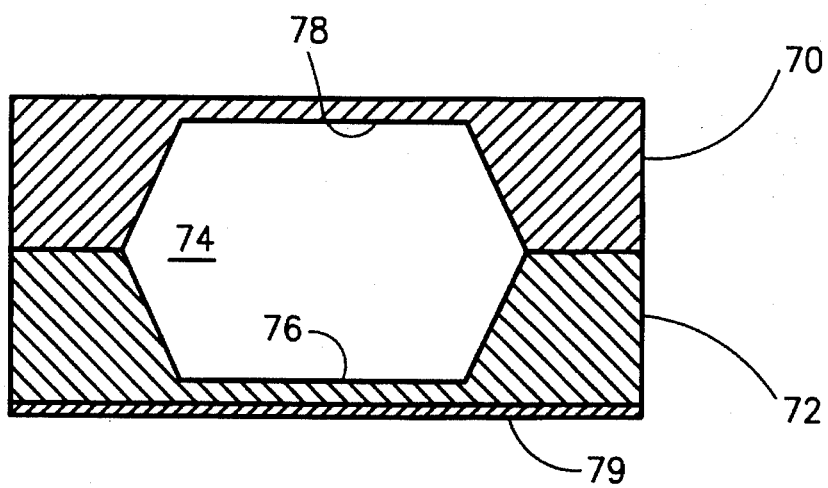
FIG. 4B is a schematic illustration of a sensor, similar to that of FIG. 4A, which is sensitive to chemical composition.

A sensor similar to that shown in FIG. 4A can be used to measure chemical composition. The resultant sensor is illustrated in FIG. 4B to which reference is now made. The thick membrane 76 of FIG. 4B is coated with a thin, soft, polymeric film 79 which absorbs gas phase analytes. The analytes add weight to film 79 and change its viscoelasticity. As a result, the vibration frequency changes.

Figure 5:
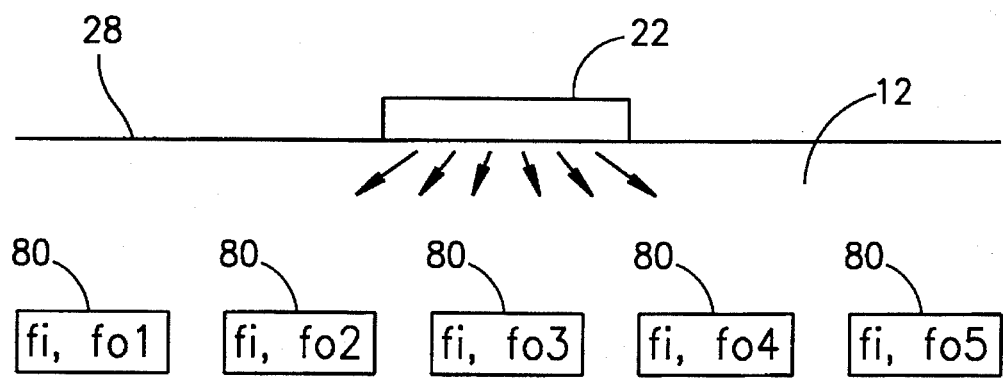
FIG. 5 is a schematic illustration of a sensor system operating with a plurality of passive sensors.

Reference is now made to FIG. 5 which illustrates a sensor system having a plurality of passive sensors 80. The sensors 80 typically have at least two vibration frequencies, an input frequency fi and an output frequency $fo_i$, where, in the example of FIG. 5, i=1 to 5. The input frequency can be identical for each sensor 80, or it can be within a predetermined range.

The output frequencies $fo_i$ are typically designed to be in separate, non-overlapping frequency ranges such that each sensor is separately detectable for all values of the physical variable being measured. In this manner, the value of the physical variable can be measured along a line, or within a region, at one time.

The sensors 80 can be formed of sensors similar to those shown in FIGS. 3 and 4. For a set of sensors similar to those of FIG. 3, the lengths of each of the long beams are of a similar length while the lengths of the short beams are significantly different. For a set of sensors similar to those of FIG. 4, the thin membranes of each are of a similar thickness but the thickness of the thick membranes are different.

It will be appreciated by persons skilled in the art that the present invention is not limited to what has been particularly shown and described hereinabove. Rather the scope of the present invention is defined by the claims which follow:

I claim:

1. A passive sensor system utilizing ultrasonic energy, the system comprising:

at least one ultrasonically vibratable sensor having at least one vibration frequency, each vibration frequency being a function of a physical variable to be sensed, said physical variable being selected from the group consisting of temperature and viscosity; and an ultrasonic activation and detection system for exciting said sensor and for detecting said at least one vibration frequency thereby to determine a value of said physical variable.

2. A system according to claim 1 and wherein said ultrasonic activation and detection system comprises:

an ultrasonic wave generator for generating an ultrasonic wave having a desired frequency band;

an ultrasonic transducer system for transmitting said ultrasonic wave and for receiving an ultrasonic wave in response; and a frequency detector for detecting said vibration frequency of said sensor from said received ultrasonic wave.

3. A system according to claim 2 and wherein said ultrasonic activation and detection system additionally comprises a data processor for converting said detected vibration frequency to said value of said physical variable.

4. A passive sensor system utilizing ultrasonic energy, the system comprising:

at least one ultrasonically vibratable sensor having at least one vibration frequency, each vibration frequency being a function of a physical variable to be sensed; and an ultrasonic activation and detection system for exciting said sensor and for detecting said at least one vibration frequency thereby to determine a value of said physical variable;

wherein said sensor includes:

a housing;

a membrane attached to said housing and responsive to said physical variable;

a vibration beam attached to said housing at one end; and a coupler, attached to said membrane and to a small portion of said vibratable beam, which bends said vibratable beam in response to movement of said membrane.

5. A passive sensor system utilizing ultrasonic energy, the system comprising:

at least one ultrasonically vibratable sensor having at least one vibration frequency, each vibration frequency being a function of a physical variable to be sensed; and an ultrasonic activation and detection system for exciting said sensor and for detecting said at least one vibration frequency thereby to determine a value of said physical variable, where said sensor comprises:

a housing;

a membrane attached to said housing and responsive to said physical variable;

a vibratable beam attached to said housing at two ends; and a coupler, attached to said membrane and to said vibratable beam at a location not close to a center of said vibratable beam thereby separating said vibratable beam into two separate but coupled vibratable beams.

6. A system according to claim 5 and wherein said sensor also comprises a reference beam attached to said housing at two ends.

7. A passive sensor system utilizing ultrasonic energy, the system comprising:

at least one ultrasonically vibratable sensor having at least one vibration frequency, each vibration frequency being a function of a physical variable to be sensed; and an ultrasonic activation and detection system for exciting said sensor and for detecting said at least one vibration frequency thereby to determine a value of said physical variable;

wherein said passive sensor has excitation and transmission frequencies;

wherein said sensor includes:

a first cup shaped body having a flat base formed of a thin membrane vibratable at said excitation frequency, and a second cup shaped body having a flat base formed of a thick membrane vibratable at said transmission frequency; and wherein said first and second bodies are jointed together so as to produce an enclosed space between them.

8. A passive sensor utilizing ultrasonic energy, the system comprising:

a plurality of ultrasonically vibratable sensors each having an output vibration frequency range which is a function of a physical variable to be sensed wherein said frequency range of each of said plurality of sensors do not overlap; and an ultrasonic activation and detection system for transmitting an ultrasonic wave having frequencies within a range covering substantially the range formed by the combination of said output frequency range of each of said plurality of sensors, thereby to excite said sensors, and for detecting output vibration frequencies thereby to determine a plurality of values of said physical variable.

9. A method of measuring a physical variable of a body, the method comprising the steps of:

activating, via an ultrasonic wave, a passive sensor located within the body and having a vibration frequency which is a function of said physical variable, said physical variable being selected from the group consisting of temperature and viscosity; and detecting said vibration frequency.

10. A method of measuring a physical variable of a body, the method comprising the steps of:

transmitting an ultrasonic wave having a first range of vibration frequencies through said body thereby to activate a passive sensor located within said body, said passive sensor having an input vibration frequency within said first range, wherein both frequencies are functions of said physical variable, said physical variable being selected from the group consisting of temperature and viscosity; and detecting said output vibration frequency.

* * * * *